United States Patent
Saylor et al.

(10) Patent No.: US 10,445,930 B1
(45) Date of Patent: Oct. 15, 2019

(54) MARKERLESS MOTION CAPTURE USING MACHINE LEARNING AND TRAINING WITH BIOMECHANICAL DATA

(71) Applicant: Southwest Research Institute, San Antonio, TX (US)

(72) Inventors: Kase J. Saylor, San Antonio, TX (US); Daniel P. Nicolella, San Antonio, TX (US); David R. Chambers, San Antonio, TX (US); Travis D. Eliason, San Antonio, TX (US); Donald R. Poole, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 26 days.

(21) Appl. No.: 15/982,691

(22) Filed: May 17, 2018

(51) Int. Cl.
*G06T 7/292* (2017.01)
*G06T 7/80* (2017.01)
*G06T 17/20* (2006.01)
*G06T 7/246* (2017.01)

(52) U.S. Cl.
CPC .............. *G06T 17/20* (2013.01); *G06T 7/251* (2017.01); *G06T 7/292* (2017.01); *G06T 7/80* (2017.01); *G06T 2200/08* (2013.01); *G06T 2207/10016* (2013.01); *G06T 2207/20081* (2013.01); *G06T 2207/20221* (2013.01); *G06T 2207/30204* (2013.01); *G06T 2215/16* (2013.01)

(58) Field of Classification Search
None
See application file for complete search history.

(56) References Cited

U.S. PATENT DOCUMENTS

| | | | |
|---|---|---|---|
| 2010/0285877 A1* | 11/2010 | Corazza | G06T 13/00 463/32 |
| 2018/0096259 A1* | 4/2018 | Andrews | G06N 3/08 |
| 2018/0357472 A1* | 12/2018 | Dreessen | G06K 9/00335 |

\* cited by examiner

*Primary Examiner* — Yanna Wu
(74) *Attorney, Agent, or Firm* — Livingston Law Firm

(57) ABSTRACT

A method of using a learning machine to provide a biomechanical data representation of a subject based on markerless video motion capture. The learning machine is trained with both markerless video and marker-based (or other worn body sensor) data, with the marker-based or body worn sensor data being used to generate a full biomechanical model, which is the "ground truth" data. This ground truth data is combined with the markerless video data to generate a training dataset.

8 Claims, 7 Drawing Sheets

MARKERLESS MOTION CAPTURE USING MACHINE LEARNING AND TRAINING WITH BIOMECHANICAL DATA

TECHNICAL FIELD OF THE INVENTION

This invention relates to motion capture systems, and more particularly to using neural networks to transform markerless video data into three-dimensional biomechanical kinematic data.

BACKGROUND OF THE INVENTION

The challenge of a motion capture system is to begin with a two-dimensional (2D) video of an animate body, and from that image sequence, to provide three-dimensional (3D) kinematic data. In other words, the motion capture system transforms 2D appearance data into 3D kinematic data.

The animate subject of motion capture can be human, animal, or any other moving body. The applications of motion capture are numerous, and include medical rehabilitation, sports, and virtual reality.

In the past, markers such as reflectors or sensors, have been placed on the subject (typically a human) under camera observation so that correspondences can be matched from 2D to 3D. However, these and other applications are greatly facilitated if there is no need for markers.

Conventionally, markerless motion capture systems use the shape and morphology of the human body to imply a virtual array of markers. The result is a 3D model, which can be combined with algorithms that express how a specific subject moves and changes shape over time.

A limitation of conventional markerless motion capture systems, as compared to marker-based systems, is accuracy of the resulting model. Existing markerless motion capture systems tend to not achieve parity with marker-based systems.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The following description is directed to a markerless 3D motion capture system that provides measurement accuracies comparable to traditional marker-based 3D motion capture systems, but requires a minimal setup time. The markerless system combines biomechanical modeling, deep neural networks, and sensor fusion techniques.

Features of the markerless system are that it may be implemented using commercial off-the-shelf video components as compared to specialized infra-red cameras used with traditional marker-based systems. A minimal number of cameras are required to capture 3D motion compared to conventional systems (one camera vs eight or more). No external markers are required to be placed on the subject. The system is easily extended to capture multiple subjects. The system provides a complete biomechanical analysis using a single system compared to multiple systems (e.g. marker-based motion capture, force plates, separate data analysis and modeling codes).

Figure 1A:
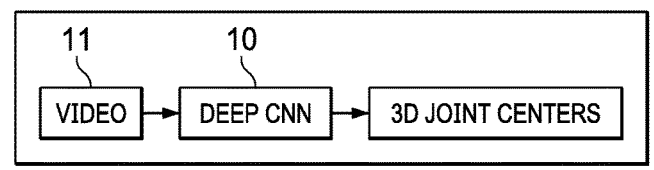
FIGS. 1A and 1B illustrate a preliminary and a final markerless motion capture system, respectively.
Figure 1B:
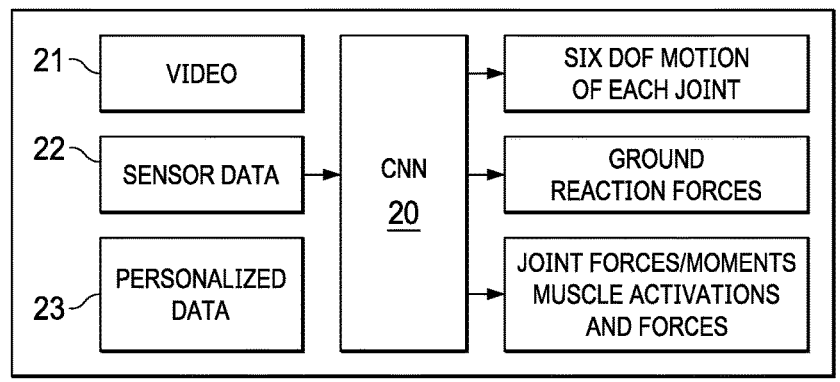

FIGS. 1A and 1B illustrate two embodiments of a markerless motion capture system. Both systems use a neural network 10 and 20 for machine learning of providing a 3D representation of an animate object from input video of the subject in motion. The system of FIG. 1A uses a deep convolutional neural network (CNN) 10; the system of FIG. 1B uses a CNN that combines the deep CNN of FIG. 1A and a recurrent NN (RNN) with fully connected layers, referred to herein as CNN/RNN 20. However, it is to be understood that the use of other types of learning machines are possible and equivalent, all being implemented with appropriate computing hardware and software.

In FIG. 1A, CNN 10 uses video data to provide 3D joint locations in each frame of the video. As explained below, deep CNN 10 is hand trained using hand labeled data. Optionally, deep CNN 10 can be training using biomechanically determined joint center locations.

In FIG. 1B, CNN/RNN 20 uses input datasets that include a video dataset 21, sensor dataset 22, and personalized dataset 23. The sensor dataset 22 is optional, and may be from any type of sensor that will help inform the CNN 20.

Figure 2:
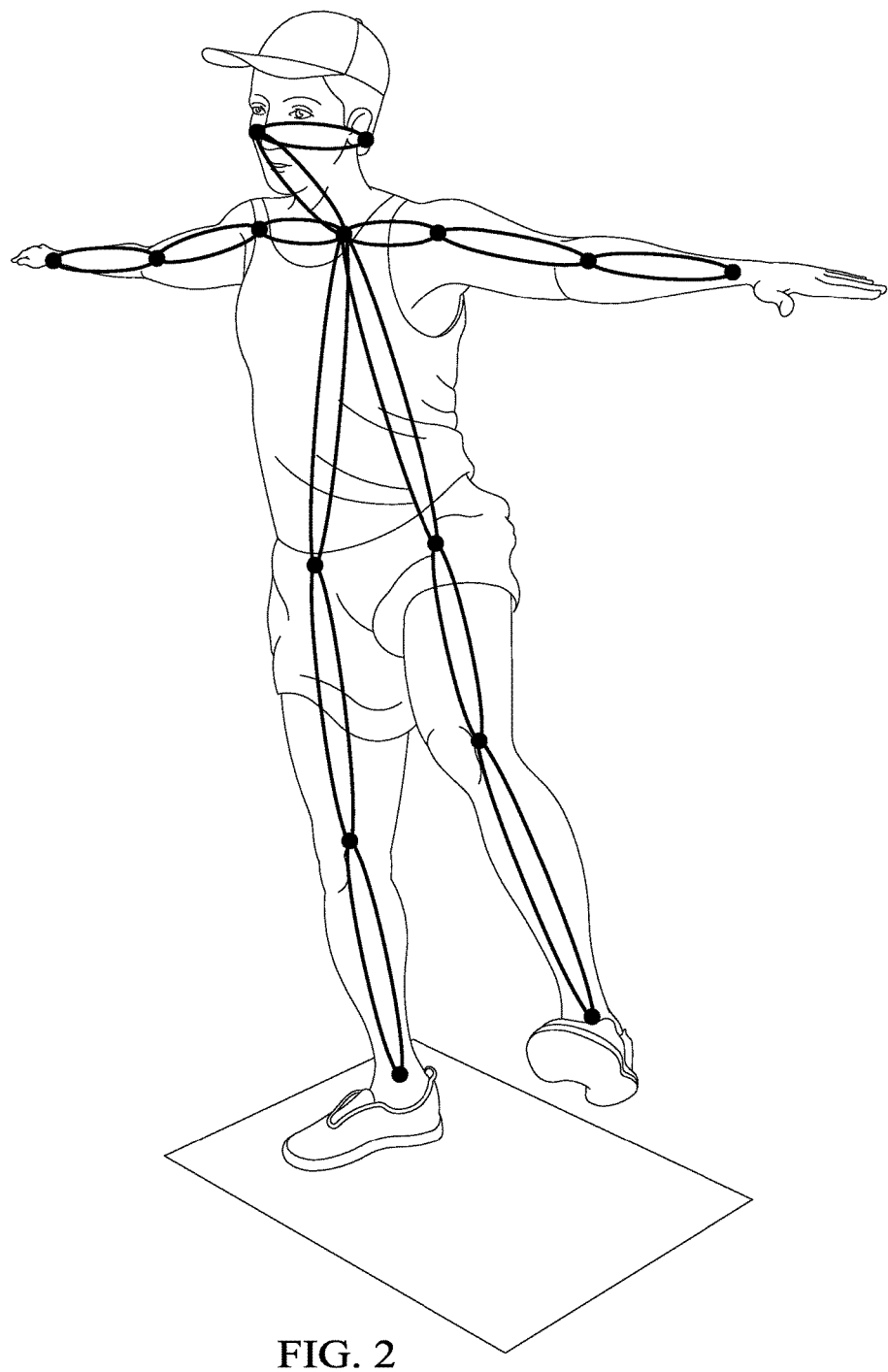
FIG. 2 illustrates joint locations predicted by the CNN/RNN of FIG. 1B.

FIG. 2 illustrates an intermediate step of CNN/RNN 20, which is joint model data similar to that provided by CNN 10. This deep CNN portion of CNN/RNN is a "2D pose machine" which predicts joint locations. If desired, these joint locations can be converted to 3D joint locations, such as by using multi-view cameras.

Figure 3:
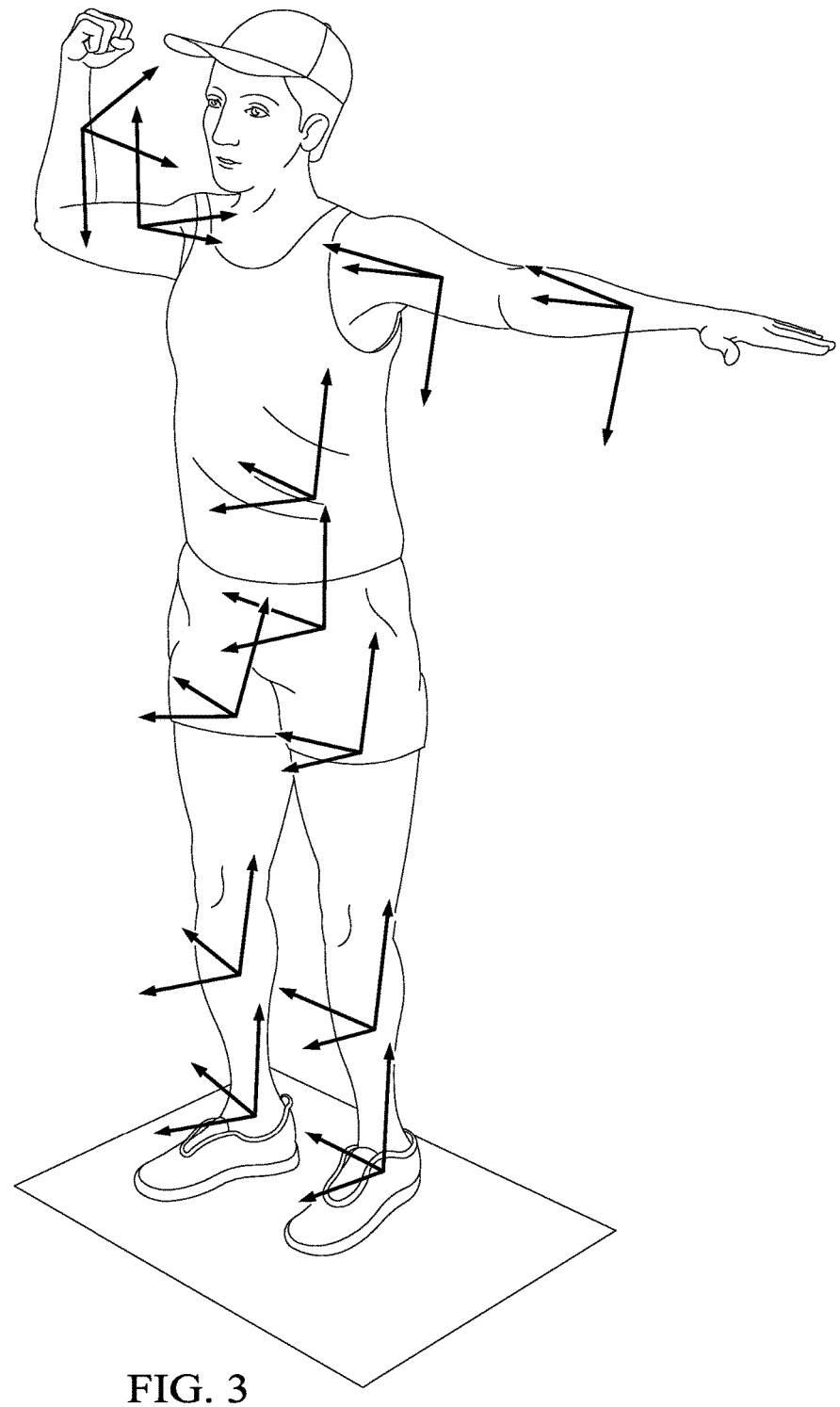
FIG. 3 illustrates the body segment orientations predicted by the CNN/RNN of FIG. 1B.

FIG. 3 illustrates the biomechanical data provided by the RNN portion of CNN/RNN 20. This RNN portion is a "3D pose machine" and uses 2D joint locations and video images to predict orientations of each body segment relative to each camera.

Figure 4A:
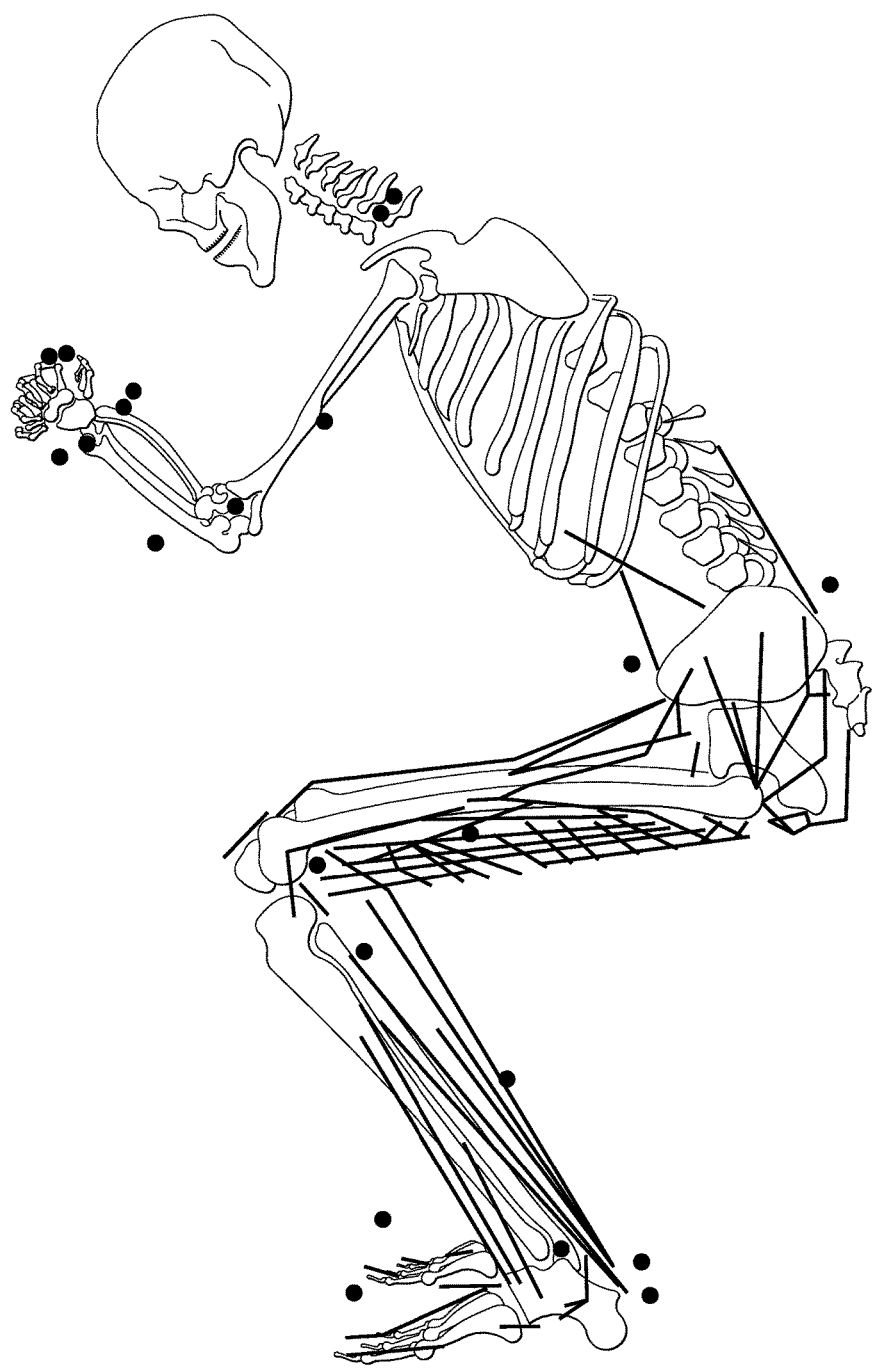
FIGS. 4A and 4B illustrate the biomechanical representation of the subject provided by the CNN/RNN of FIG. 1B.
Figure 4B:
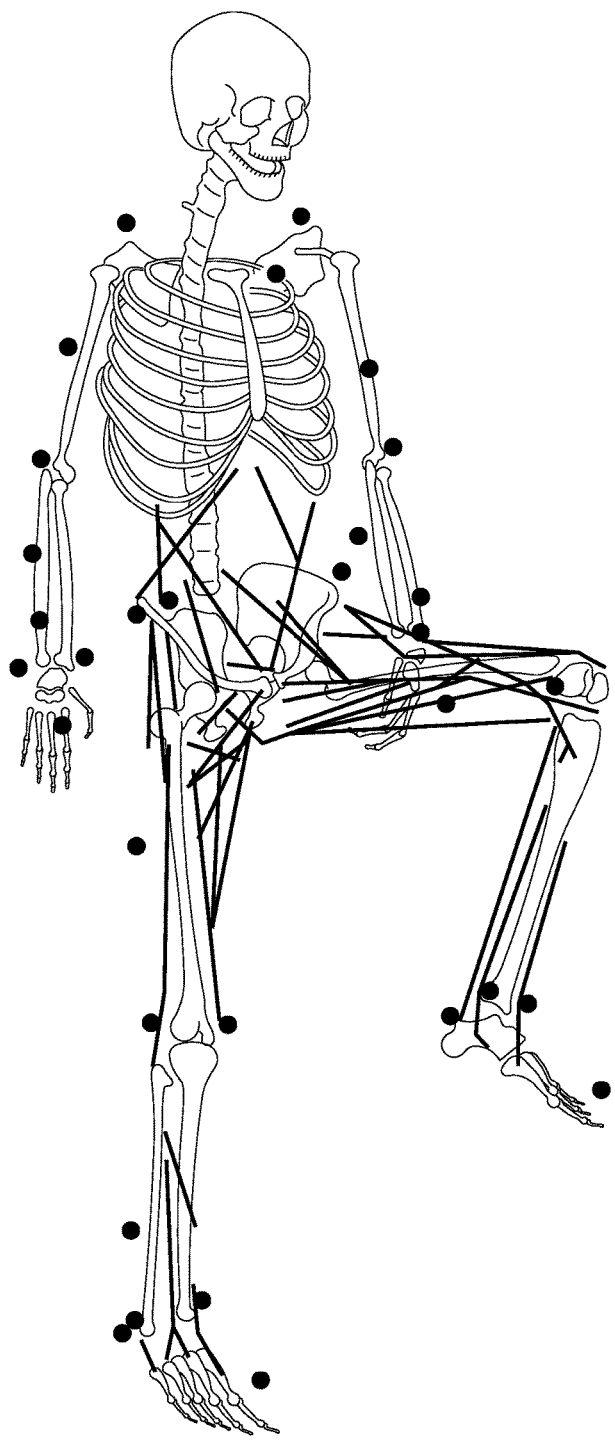

FIGS. 4A and 4B illustrate how the relative rotations of the different body segments are used to reconstruct the biomechanical state of the subject. The results from the system of FIG. 1B is a full-body biomechanical representation of the subject. It provides data representing joints with six degrees of freedom (DOF), ground reaction force data, and data representing forces and moments of joints and muscles.

The training of both CNN 10 and CNN/RNN 20 is described in detail below, with the training of CNN 10 being described as an initial step in the training of CNN/RNN 20.

CNN/RNN Training Dataset

CNN/RNN 20 is trained using a biomechanically correct "ground truth" training dataset. A marker-based motion capture system is used to capture video data. Using data from the marker-based motion capture system, a complete, subject-specific, model-driven biomechanical motion analysis is performed for each motion capture session of each subject. Alternatively, an inertial measurement unit (IMU) based motion capture system can be used in place of the marker-based motion capture system to generate the data for the subject-specific biomechanical model.

The output of this analysis is a complete 3D kinematic description of each model-defined body segment, and this data serves as the training data set for CNN/RNN 20. Then, the output of the trained CNN/RNN 20 is equivalent to the output from the model-driven biomechanical motion analysis.

The marker-based motion capture system uses infra-red (IR) markers and IR cameras, but other marker-based or body-worn sensor systems may be used. To train with video data comparable to biomechanics data produced by the marker-based capture system, a video capture framerate greater or equal to 100 frames per second (FPS) marker-based is used. USB3-based cameras may be used to achieve the desired frame rates, and are able to achieve a frame rate of 396 FPS or higher.

USB3 cameras result in a significant amount of data captured, and with the abundance of data and the structure of the neural network, overfitting of the network to a fixed subject orientation is addressed by replicating each motion capture session using three separate subject orientations. This creates enough differentiation in each take to create a more resilient neural network for different subject alignments.

Training data is acquired for multiple individuals, with a validated biomechanical model for each individual. The use of these validated biomechanical models allows the CNN/RNN 20 to surpass "animation grade" motion capture and provide results that go beyond simply locating the 3D spatial location of hip and knee joints, to measuring the 3D position of each joint as well as the three independent rotations of the interposed body segments (e.g. flexion, abduction and rotation of the femur).

For the CNN/RNN 20 of FIG. 1B, new machine learning structures are used to improve the initial markerless motion capture system of FIG. 1A. First, an initial CNN was trained to predict joint center locations. Then CNN/RNN 20 was trained to estimate the kinematic state from the 3D joint locations, demonstrating the ability to map a reduced set of body points (a simplified input) to the full biomechanical state in the context of natural movements.

Furthermore, a framework for modeling the human body kinematic chain in order to model body segment orientations was developed. This new framework provides additional outputs from a revised joint location CNN, one which predicts the full orientation of body segments with respect to the camera. This new output enables the retrieval of a full biomechanical state without the need for establishing additional body points (i.e., beyond the joint locations). By introducing the concept of body orientation to the neural network, the resulting network output provides the same number of degrees of freedom as conventional biomechanical models that require dozens of physical markers to be placed at precise points on the test subject.

The overall procedure for training CNN 20 is improved by fusing data from a motion capture system and a machine vision camera system. First, the motion capture system and the camera system are calibrated together. This entails calibrating cameras to correct for lens distortion and using multi-view geometry to determine the transformations between the machine vision cameras and the motion capture system origin. Second, an action sequence, known as a "take," is captured, simultaneously with both the machine vision system and the motion capture system. A trigger signal is used to ensure time synchronization. Next, the motion capture data is used to fit a kinematic model using software that produces joint locations in the motion capture coordinate system as well as the joint angles, or kinematic state, of the subject at every time-step. An example of suitable software is OpenSim. Finally, the kinematic state data is aggregated into a common file with the (markerless) machine vision data to produce a single file that stores all relevant data for the take. Such files, representing a number of different subjects and actions, form a database used to train CNN/RNN 20. Using the camera properties and the known transformations to the motion capture coordinate frame, the 3D joint locations and other information can be projected into the camera's frame of reference and used to train CNN/RNN 20 for markerless motion capture. This approach automates as much of the training steps as possible, and, thereby, enables a more rapid approach for adding training data to the overall training set in the future.

Figure 5:
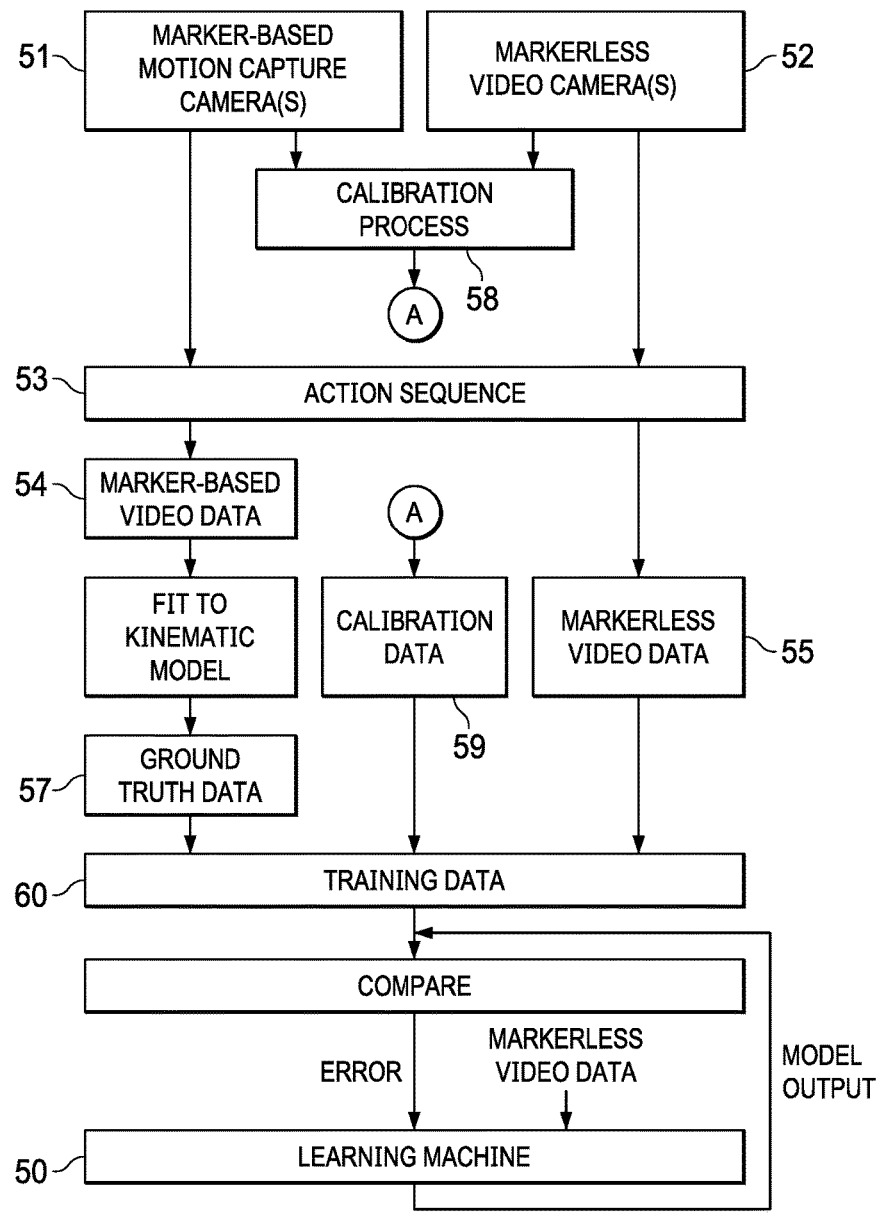
FIG. 5 illustrates a method of training a learning machine to provide a biomechanical representation of a subject.

FIG. 5 illustrates a method of training CNN/RNN 20, or other machine learning model 50 for markerless motion capture in accordance with the invention. As explained above, it should be understood that the use of a "neural network" is for purposes of example, and the method may be implemented with other types of machine learning models, all using appropriate computing equipment.

A marker-based motion capture camera (or multiple cameras) 51 is used to capture video data of the animate subject. Markers are placed on joint locations of the subject. For purposes of example, the marker-based camera(s) use infra-red markers and camera(s). other types of motion capture systems may be used to capture the ground truth motion training data.

A markerless motion capture camera (or multiple cameras) 52 is also used to capture video data of the animate subject.

In Step 53, the two sets of cameras 51 and 52 are simultaneously used to capture their respective video data of the subject in action. The result is a dataset of marker-based video data 54 and a dataset of markerless video data 55.

In Step 56, as described above, the marker-based video data is fit to a kinematic model. The subject's personalized data may also be factors in the model. The result is a dataset of ground truth data 57.

In Step 58, the marker-based camera(s) 51 and the markerless camera(s) 52 are calibrated as described above. The result is a set of calibration data 59.

In Step 60, the calibration data 59, the ground truth data 57, and markerless data 58 are calibrated together and combined into a training data set.

The collection of training data is repeated for multiple subjects, performing different motions. Thus, the above-described steps are repeated for different subjects and different action sequences. Each subject is fit to a kinematic model, and the model data is combined into the ground truth data set 57.

After ground truth dataset 57 has been collected, the markerless video dataset 55 is used as input to the machine learning model 50. The outputs are compared to the training data, and an iterative comparing an adjusting process is used to train the model 50.

Referring again to FIG. 1B, once the CNN/RNN 20 is trained, to provide a complete, end-to-end, biomechanical analysis using only cameras, the final system follows the following steps:

1. Each subject has associated personal data, such as height, weight, and strength parameters. The subject's motion is captured by cameras and each image is run through a 2D pose machine to identify joint locations. If desired, these can be triangulated to 3D using multi-view.

2. A novel 3D pose machine uses the resulting 2D joint locations and the images to predict the orientations, expressed as quaternions, of each body segment relative to each camera.

3. The relative rotations of the different body segments are used to reconstruct the biomechanical state of the subject from each camera.

4. Fused predictions from multiple cameras are done with mean or median filtering (this could be done via a neural network, but is currently done as separate step).

The result from the system is a full-body biomechanical representation of the subject.

As shown in FIG. 1B, the CNN/RNN 20 may be trained to receive and use various biomechanical sensor data 22 to better inform the biomechanical representation of the subject.

Figure 6:
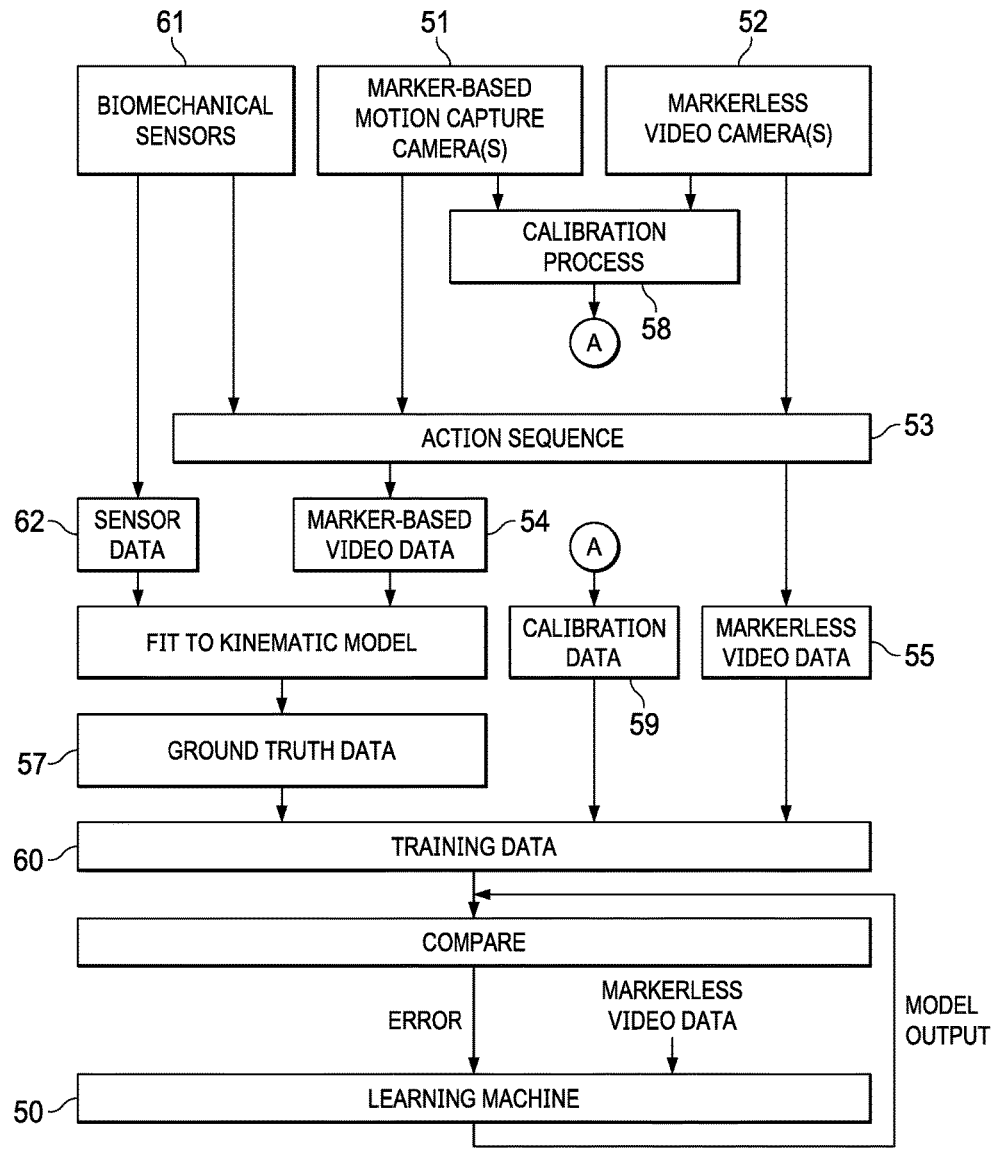
FIG. 6 illustrates the training method of FIG. 5, enhanced to include training with one or more types of biomechanical sensors.

FIG. 6 illustrates an enhanced training process that includes the use of one or more biomechanical sensors. In Step 61, the subject is outfitted with one or more types of these sensors. Such sensors can include force plates, electromyographic (EMG) sensors, accelerometers, magnetometers, and gyroscopes such as inertial measurement units (IMUs), and are placed on or near the subject as is appropriate for the sensor. The action sequence performed in Step 53 includes the use and collection of data from these sensors, as well as acquiring the video data from the two sets of cameras 51 and 52.

Examples of the resulting biomechanical sensor data 62 are ground reaction forces, muscle activation data, and IMU data. This data is integrated into the biomechanical model data 56, and becomes a part of the ground truth data 57 used for training.

What is claimed is:

1. A method of training a learning machine to receive video data captured from an animate subject, and from the video data to generate biomechanical states of the animate subject, comprising:
    placing markers on the animate subject;
    using both marker-based motion capture camera(s) and markerless motion capture camera(s) to simultaneously acquire video sequences of the animate subject, thereby acquiring marker-based video data and markerless video data;
    wherein the marker-based camera(s) detect the markers on the animate subject in a manner differently from detection of the rest of the animate subject;
    fitting the marker-based video data to a kinematic model of the animate subject, thereby providing a ground truth dataset;
    combining the ground truth dataset with the markerless video data, thereby providing a training dataset;
    inputting the markerless video data to the learning machine;
    comparing the output of the learning machine to the training dataset;
    iteratively using the results of the comparing step to adjust operation of the learning machine; and
    using the learning machine to generate at least one of the biomechanical states of the animate subject.

2. The method of claim 1, wherein the combining step is performed by calibrating the marker-based motion capture camera(s) and markerless motion capture camera(s) and using the results of the calibrating to generate the ground truth dataset.

3. The method of claim 1, wherein the placing, using, fitting, and combining steps are performed for multiple animate subjects.

4. The method of claim 1, wherein multiple animate subjects perform different activities.

5. The method of claim 1, further comprising the step of installing one or more biomechanical sensors on or near the animate subject, and wherein the output of the one or more biomechanical sensors is used to generate the kinematic model.

6. The method of claim 5, wherein the one or more biomechanical sensors are one or more of the following: force plate, electromyographic sensor, accelerometer, or gyroscope.

7. A method of training a learning machine to receive video data captured from an animate subject, and from the video data to generate biomechanical states of the animate subject, comprising:
    placing one or more biomechanical sensors on the animate subject;
    using both sensor detector and markerless motion capture camera(s) to simultaneously acquire video sequences of the animate subject, thereby acquiring sensor detector data and markerless video data;
    wherein the sensor detector data is data that acquired by detecting the one or more biomechanical sensors as the animate subject moves;
    fitting the sensor detector data to a kinematic model of the animate subject, thereby providing a ground truth dataset;
    combining the ground truth dataset with the markerless video data, thereby providing a training dataset;
    inputting the markerless video data to the learning machine;
    comparing the output of the learning machine to the training dataset; and
    iteratively using the results of the comparing step to adjust operation of the learning machine; and
    using the learning machine to generate at least one of the biomechanical states of the animate subject.

8. The method of claim 7, wherein the one or more biomechanical sensors are one or more of the following: force plate, electromyographic sensor, accelerometer, or gyroscope.

* * * * *